US009241630B1

(12) United States Patent
Watkins

(10) Patent No.: US 9,241,630 B1
(45) Date of Patent: Jan. 26, 2016

(54) AUTO ATTENDANT SYSTEM WITH RESPONSE VERIFICATION AND MEMORY-INDUCING COMPONENTS

(71) Applicant: Frazier Watkins, Memphis, TN (US)

(72) Inventor: Frazier Watkins, Memphis, TN (US)

(*) Notice: Subject to any disclaimer, the term of this patent is extended or adjusted under 35 U.S.C. 154(b) by 0 days.

(21) Appl. No.: 13/668,385

(22) Filed: Nov. 5, 2012

(51) Int. Cl.
*A61B 5/00* (2006.01)
*G08B 21/04* (2006.01)
*G06F 19/00* (2011.01)

(52) U.S. Cl.
CPC ............ *A61B 5/0002* (2013.01); *A61B 5/0022* (2013.01); *A61B 5/7425* (2013.01); *A61B 5/7435* (2013.01); *G08B 21/04* (2013.01); *G06F 19/3418* (2013.01)

(58) Field of Classification Search
CPC ........................ A61B 5/0002; A61B 5/0022
USPC ............ 340/573.1, 573.4, 505, 506; 700/247, 700/258, 259; 705/3, 326; 348/46, E13.074
See application file for complete search history.

(56) References Cited

U.S. PATENT DOCUMENTS

| 7,222,000 B2* | 5/2007 | Wang et al. .................. 700/259 |
| 8,340,819 B2* | 12/2012 | Mangaser et al. ............ 700/253 |
| 2007/0174079 A1* | 7/2007 | Kraus ................................ 705/1 |
| 2012/0212582 A1* | 8/2012 | Deutsch ......................... 348/46 |

* cited by examiner

*Primary Examiner* — Van Trieu
(74) *Attorney, Agent, or Firm* — William S. Parks; Hulsey, Hunt & Parks, PC

(57) ABSTRACT

A mounted or portable device that allows for instant communication and notification between two parties is provided. Directed primarily at elderly family members and the like that live on their own, such a device includes a video screen for display of various media in order to provide memory inducements, as well as video communication on demand. Furthermore, such a device permits a remote user to contact the person with a request for instant verification of the person's condition. Failure to respond to such a request leads to automatically sent communications to pre-assigned recipients that attention for the person user may be required, thereby seeking the closest recipient proximally at that specific moment to provide such attention and/or notification to proper authorities that medical or other help is needed. The system also allows the direct user the capability of contacting medical/police/etc. authorities if attention is needed immediately as well.

3 Claims, 2 Drawing Sheets

AUTO ATTENDANT SYSTEM WITH RESPONSE VERIFICATION AND MEMORY-INDUCING COMPONENTS

FIELD OF THE INVENTION

The present invention relates to a mounted or portable device that allows for instant communication and notification between two parties. Directed primarily at elderly family members and the like that live on their own, such a device includes a video screen for display of various media in order to provide different memory inducing scenes, as well as video communication on demand through an automatically activated preprogrammed clip. Furthermore, such a device permits a remote user to contact the direct user with a request for instant verification of the direct user's condition. Upon failure to respond to such a request, the overall system automatically sends communications to all pre-assigned recipients that attention for the direct user may be required, thereby seeking the closest recipient proximally at that specific moment to provide such attention and/or notification to proper authorities that medical or other help is needed. The system also allows the direct user the capability of contacting medical/police/etc. authorities if attention is needed immediately as well. Overall, the inventive system provides an all-inclusive device to help elderly or otherwise handicapped or mentally challenged persons and/or patients with a variety of beneficial activities, communication capabilities, and notification processes to aid in such a direct user's well-being and safety. The method of utilizing such a device for such various end-uses is also encompassed within this invention.

BACKGROUND OF THE INVENTION

Difficulties arise as the population ages around the world. With improvements in medical technology, life spans increase leaving a greater number of elderly persons that require a certain degree of attention to assure that everyday activities and general health issues are acceptable for such a population segment. Additionally, such aging members of society do not commonly seek living arrangements in a nursing home facility or communal location. Although some elderly persons are placed in such around-the-clock and/or close-quarter situations, many others desire to live in their own homes or apartments, whether it be for financial, logistical, or other reasons. It has further been well-documented that short-term memory loss may be reduced for patients that remain in familiar surroundings and, even with removal from such an environment for as short as a few days, such a patient may suffer unfortunate consequences in this manner. Thus, the benefits of having elderly or other patients susceptible to short-term memory loss issues staying in their own homes are quite substantial. As such, family and friends generally seek suitable methods of monitoring such self-sustaining elderly, etc., persons to ensure safety and health concerns are properly met.

Furthermore, there are people within a narrower segment of society that face the unfortunate issues of early onset dementia while also desirous of sustaining his or her own household. Such a situation may not automatically cause a caregiver or family member to seek professional help, such as a nursing home or like facility, for constant monitoring and safety issues; actually, with early onset of such a disease or condition (such as, for example, Alzheimer's) a patient may exhibit short-term memory loss or other reduction in mental capacity at that point and certain activities or therapeutic methods utilizing the patient's mental faculties may help to prevent further deterioration. Constant presence of a caregiver for such a purpose may prove too expensive for such an endeavor. As well, the lack of a familial subject to aid in such a mental exercise through voice and visual commands and/or stimulations militates against the utilization of an outside subject for such a purpose in many situations. However, the constant presence of a family member (or like close friend, as one example) may not prove feasible, either, as such a person may not have the time, resources, and wherewithal to provide such around-the-clock attention. Memory stimulation from a suitable source may thus provide the desired therapeutic effect while allowing the patient to remain in their own familiar surroundings.

As such, there exists a definite need to provide a beneficial system, method, and/or device that allows for constant monitoring as well as providing potential therapeutic mental exercises for a patient. Such a device should not rely solely on the patient's input or activity in order to enable a monitoring system to operate. Likewise, such a system should not prove appreciably invasive into the patient's life (through, for example, constant video monitoring). Additionally, any constant video monitoring would prove extremely difficult for a monitor to undertake throughout an entire day, not to mention the privacy issues the patient would not want to lose. As a result, any such system would necessarily allow for an interested and authorized party to elicit a proper response from the patient directly through the system, as well as the capability to either generate on demand a mental exercise program or the ability of such an interested and authorized party to set up a pre-scheduled session (or multiple daily sessions) of such a mental exercise program for the patient's benefit.

In the past, and up to today, the industry that pertains to helping monitor family members has centered on broad tracking, video viewing, and/or self-reporting devices. For instance, personal tracking devices have been found to be useful in locating missing persons. Such tracking devices typically use a network of Global Positioning Satellites (GPS) in low earth orbit that broadcast precise timing signals from on-board atomic clocks. Using triangulation formulas, a device that picks up signals from several satellites simultaneously can determine its position in global coordinates, namely latitude and longitude. Thus, an object and/or person carrying the GPS device may be located provided the appropriate equipment and trained personnel are available for determining the location of the GPS device. Such devices are clearly limited to situations that concern placement of proper reporting/monitoring phones, computer chips, and the like, and offer after-the-fact help once a person has gone missing. Such devices also provide nothing beyond a tracking benefit; therapeutic and/or responsive reporting is unavailable.

There are standard systems in place today that include audio as well as, in some circumstances, audiovisual communications, in nursing homes and like facilities. Such devices are used primarily as communication devices as well as for emergency notification purposes. Beyond that, however, such systems are rather limited in that communications are reliant upon the activity of a patient/tenant and are generally located in specific facilities. Otherwise, the utilization of cell phones and/or computers serve much the same purpose. In terms of providing overall services for patients suffering from dementia, memory loss, or other like symptoms, there is no component within such systems and processes that takes into account such a specialized type of situation. With the potential for decreased mental capacity, a patient's ability to properly operate and/or activate such a device is highly suspect. Such a lack of direction in that respect thus limits the usefulness of such a typical communication system and leaves a rather significant portion of society without suitable offerings to not only help such patients in terms of therapeutic benefits, but do not allow for automatic notifications if lack of communication from a patient occurs.

Likewise, there are devices that patients may keep with them constantly to permit instant notification of health problems. Such devices that are worn by a user for the purpose of instantaneous notification of health or status difficulties have been utilized for many years. Although such devices may provide a certain degree of comfort to both user and family members (or friends) that reports of such problems may be handled quickly and reliably, such may not be the case with patients suffering from certain degrees of memory loss and other dementia maladies. In actuality, the requisite active nature of such self-reporting devices forces the user to remain vigilant, both in terms of remembering the availability, if not presence, of such a signal device on their person, but the failure of activation likewise prevents proper communication with the necessary authorities and/or family members that any problem is at hand. These devices thus fail to permit an outside party from communicating with the user and thus relies solely upon the user's capacity to understand and activate the device itself. Again, in situations with dementia patients, at least, such a requirement is deficient as to the reliability such a system actually provides all parties involved.

As it stands, although certain systems do exist to allow for both communication with patients in homes, rooms, and other like locations, these are limited to communication alone. There is no consideration with the importance that memory stimulating programs can provide (particularly in a potentially therapeutic environment for early onset dementia patients) in addition to communication capabilities. Likewise, mere distress reporting devices do not allow early onset dementia patients full potential in terms of reliability that status reports will be made timely and properly. The ability to compensate for such reliability deficiencies, as well as the capability of providing at least a combination of therapeutic memory stimulation programs and status reports from such patients to any number of authorized interested outside parties would be highly beneficial to this growing segment of society. As of today, however, such a system and/or device is unavailable within the remote report/dementia patient treatment industry.

ADVANTAGES AND DESCRIPTION OF THE INVENTION

The present invention thus provides the advantage of simultaneously offering a monitoring device and system and a video presentation (or presentations) in order for a person located at the same location as the device and system to experience the benefit of programmed video messages for both therapeutic and monitoring purposes. Another advantage is that a remote party may have such a device and system programmed such that upon activation of such a video message the monitored party is then reminded to communicate his or her status in response thereto. Additionally, the system and device offer the advantage that any lack of timely communication of status in response to such a message will create a stream of communications to authorized monitoring persons in order to ensure the monitored party's health and safety is in order. Still another advantage of such an invention is the capability of providing such a device in a stationary location or in a portable situation, as well as the potential to utilize on-line systems, wi-fi arrangements, telephone lines, and any other like communication channel to permit all such communication actions. As well, the ability for an authorized remote monitoring party to program and/or activate the system and device on demand and for such a purpose as to either stimulate the memory capacity of the monitored party, request an update as to the monitored party's status, or both, is yet another noticeable and important advantage such an inventive system and device allow.

Accordingly, the invention encompasses a combination memory stimulation/communication system for utilization with a remote patient, wherein said system comprises a device including: a) a video presentation component comprising at least i) a video screen for presenting visual pictures and/or films to a remote patient, wherein said visual pictures and/or films are set to repeat on said video screen, and ii) a stop or reset switch to permit said remote patient to discontinue the video presentation; b) a communication component comprising at least i) a communication module to allow for spoken communications to transfer between said remote patient and an authorized outside party, and ii) an alarm and signal generator to notify an authorized outside party of the failure of said remote patient to timely activate said stop or reset switch of step a)ii); and iii) an override component available to said at least one authorized outside party to discontinue said alarm and signal generator upon receipt of a suitable communication from said remote patient subsequent to alarm and signal generator activation. Said invention thus also encompasses the overall method of providing a memory stimulation presentation to said remote patient through the utilization of said video screen through the activation of a program including at least one visual picture or film, wherein said memory stimulation presentation is coupled to a stop or reset activation switch to be operated by said remote patient upon receipt of said memory stimulation presentation; said method further comprising the step of notifying at least one authorized outside party of the failure of said remote patient to activate said stop or reset activation switch within a suitable amount of time subsequent to initiation of said memory stimulation presentation, wherein said at least one authorized outside party may then discontinue said notification step upon receipt of a proper communication with said remote patient.

As noted above, such an inventive system/device/method allows for any number of people to remain in their own homes with a reliable method of communication and notification if any problems ensue in such a situation. Early onset dementia, in particular, has proven rather troublesome to handle for many people. Such patients do not exhibit long-term problems with memory loss or other typical dementia issues, and thus would like to enjoy the independence of their own surroundings while also having security that should any health or safety issues arise then such people (patients) can rely upon the inventive system to notify loved ones or other authorized persons to help. Additionally, though, the issues involved with early onset dementia (or early onset Alzheimer's, or other like conditions) leave such persons prone to memory loss that may actually be treated through certain therapeutic activities, such as, for instance, repetitive or long-term presentations of pictures of family members or other close acquaintances, as well as films or other video presentations of certain settings, activities, remembrances, and the like. In such a manner, it has been found that such patients may, through such presentations, exhibit proper stimulation of motor neurons and other brain activity that enhances and, at least, curtails memory loss in many such patients. With early onset cases, then, the ability to provide such an effect, particularly through a remote control system, or, otherwise through a pre-programmed device, accords such a patient with an effective manner of memory stimulation in a regimented fashion, such as daily, every few hours, even hourly (the regimen may be programmed in any manner to effectuate any time interval for such a memory stimulation presentation).

Although there are other devices that accord memory stimulation activities, there are none that combine such an action with a status notification method as well. As such, the utilization of the inventive device/system may be undertaken at any location that allows for a remote patient (i.e., an early onset dementia patient, or one exhibiting a similar condition, as described above) to enjoy a certain degree of independence, such as his or her own home or apartment. As such, although community living centers and nursing home facilities may be equipped with such a device, the versatility of such a system/device allows greater freedom and reliability when put into practice. The potential for a remote patient then to have such a memory stimulation event initiated in a regimental fashion provides only one portion of the overall system/device benefit and effect.

Additionally, then, and importantly, the system/device accords the remote patient and an authorized outside party (such as, for instance, a family member or a friend that has been added as a person to be contacted in association with the overall system/method herein described) the security that not only is the remote patient being presented memory stimulation activities, but also a notification step wherein the remote patient must acknowledge receipt of the message and thus stop or reset the memory stimulation presentation within a certain time frame or else the system sends an alarm or signal to all authorized outside parties that such an action has not properly occurred. Such a request for acknowledgement by the remote patient may thus be included within the video clip presentation or generated automatically by the device itself and provided in video, audio, or both formats. In this manner, the memory stimulation activity serves not just as a therapeutic basis for the remote patient, but also indicates the proper time for such a patient to activate a notification switch (i.e., the stop or reset switch) that translates from such an inactivation step to a reliable notification step that instructions from the memory stimulation presentations have been understood and followed by the remote patient. Thus, in this manner, the remote patient actively indicates to all authorized outside parties that not only is he or she participating in the memory stimulation activity as per the set regimen, but also that he or she is not in trouble from a safety or health perspective. If the system/device activates the memory stimulation presentation and there is no inactivation step undertaken by the remote patient within a predetermined time frame subsequent to activity initiation, then the system/device activates an alarm or signal that provides notification as soon as possible to all authorized outside parties that a failure to act on behalf of the remote patient has occurred. At that point, all such persons may then set about to contact any authorities (police, ambulance services, etc.) or other persons that are located in close proximity to the remote patient (or, of course, contact one another and/or travel to the remote patient's location) in response to such a system/device notification. Overall, the system/method/device thus provides an effective combination of memory stimulation activity and status notification process to both treat and ensure the safety and health of a remote patient.

Additionally, the overall system/method includes the capability for an authorized outside party to discontinue the notification process if, upon receipt of a proper communication from the remote patient that meets the outside party's own criteria of suitable status. The system/device may thus include a communication component that allows for such direct remote contact, through telephonic or audiovisual components.

The system thus includes a video screen, preferably of an Liquid Crystal Display (LCD) type (although any type of such visual display may be utilized, including plasma, transistor, vacuum tube, etc., technologies), and preferably conveying color to the remote patient. Such a screen would have the capability of presenting pictures, movies, basically any typical visual presentation, on demand, or through a programmable system. Additionally, the video screen should be coupled to a sound card or like device to permit correlated sound to any such video presentation. Such a presentation may thus include a pre-recorded soundtrack to accompany a picture, a set of pictures, a film, a set of films, etc., or may have a film with an accompanying soundtrack. In other words, any situation of the type that allows for the remote patient to enjoy a proper viewing with accompanying sound therewith to enhance the memory stimulation activity. The device should also allow for sound to be transferred through the proper channels if such a device is utilized for the purpose of communicating with an authorized outside party, not to mention, if desired, with a suitable authority if the remote patient utilizes such a system/device to contact the police, hospital, ambulance service, etc., if necessary. In essence, the system/device includes a proper audiovisual component for video presentations with sound, as well as for the purpose of communication with outside parties. Additionally, then, if desired, and if the outside party at issue has similar capabilities with their own communication device, the audiovisual component may be configured to allow for video calls (such as through SKYPE®-like devices) with such persons.

Furthermore, the system/device would also include at least specific buttons or other like indicators for the remote patient to press related to specific actions. Thus, for instance, a red button may be present to indicate an emergency, a green to indicate all is in a safe state, and the like. Additionally, however, the system/device may also include a numeric keypad for the remote patient to properly dial telephone numbers, if necessary. If desired, as well, such a keypad may be expanded to include an entire QWERTY keyboard if the remote patient were so inclined to utilize such for communication purposes. To that degree, then, the overall communication capability of such a system/device may be expanded to include texting and like processes for such a purpose, dependent, certainly, upon the capacity and physical capability of the remote patient to such an extent.

The basic device/system then will include a computer component that properly stores and, upon activation through any number of stimuli, initiates the video presentation as needed to accord with the remote patient's memory stimulation activity regimen. The computer is programmed either through an embedded chip or added program (through a disc or other type of device), or the system may allow for an authorized outside party to initiate such a visual presentation from a remote location on demand. The important issue is that the remote patient is notified that such a presentation is initiated and thus attention and participation therein is necessary (specifically to then allow for the notification step to occur in a timely fashion). To achieve this, the system may also include an alarm that alerts the remote patient through the device itself (such as a proper loud and/or repetitive noise or a lighting display) or possibly through a remote notification device that the remote patient keeps on their person. Alternatively, the device may be set up in multiple rooms of a dwelling for simultaneous activation to reduce the movement required of the remote patient to experience the overall memory stimulation activity, or proper notification devices may be planted in multiple rooms of such a dwelling to notify the remote patient that such an activity is to start shortly. In that manner, lights or alarms may be remotely configured around such a dwelling to provide lighted, sound-based, or both, notifications to the remote patient of such an issue. In any event, again, the important issue is that the remote patient understand that once the presentation is initiated, participation is expected such that further instructions can be provided that need to be understood and proper steps then undertaken to ensure that inactivation of the system to prevent notifications to authorized outside parties.

Thus, the computer will initiate such a memory stimulation activity, including the audiovisual clip (picture, film, or both, for instance) until the remote patient activates the proper switch to discontinue such a clip. Such a clip may include a calm, reassuring, and friendly greeting to the remote patient as a means to comfort such a person to aid in the memory stimulation process. For best results in terms of memory stimulation, it has been found that, as noted above, videos and pictures of family members and/or friends enjoying certain activities themselves (such as, as one non-limiting example, a video of grandchildren skiing down a familiar slope) coupled with a recognizable voice narrating such a clip with pertinent information and facts regarding all persons present within such a clip, are particularly viable for such a purpose. If the clip repeats too many times, or if the clip's instructions (such as a voice command telling the remote patient to activate such a switch within a certain amount of time), then the computer component will then, through a programmed resource, activate an alarm and signal generator to communicate that a lack of such activity has occurred. To that end, the computer may then undertake any number of possible actions to notify authorized outside parties (at least one such person) of such an issue. Thus, the computer may seize the phone line (particularly if it is currently in use) and dial multiple pre-set numbers for all such outside parties. The parties would then receive a standard message indicating, in some fashion, that the remote party may have a health or safety-related issue that requires immediate attention. Such a messaging service from the system/device would continue until either the remote patient has provided a communication to an authorized outside party that his or her status is acceptable, or until an outside party has arrived at the dwelling of the remote patient to personally validate such a status. In either situation, the outside party at issue would then either remotely or in person activate a proper switch to discontinue such messages or generate a preprogrammed message to send to all such outside parties that the situation is acceptable and safe. Any communications with such an authorized outside party from the remote patient may be undertaken through the inventive device, as noted above, such as utilizing the keypad for a telephonic and/or audiovisual communication step to that effect. Likewise, all such communications from the computer to all authorized outside parties may be accomplished through emails, instant messaging, computer-generated texting, and all other available outlets for such a process.

Such communications may be undertaken by any number of a variety of instruments and devices. Telephonic means (through land lines, for example) are possible, as described above. Additionally, though, wireless means may be implemented and utilized for such purposes. For instance, the remote patient may have a portable device or, preferably, at least in one non-limiting embodiment described herein, a wall- or furniture-mounted device that includes a single or bi-directional wireless communication link for transmitting information therefrom to any number of outside parties (through their cellular phones, computers, and the like) via a local hub or receiving station or base station server by way of a wireless radio frequency (RF) link using a proprietary or non-proprietary protocol. For example, within the remote patient's dwelling, a mesh network signal transferring device may be present to send and receive wireless signals Systems having any of the above-described apparatuses in combination with other computer devices, for example, to form a local area network (LAN), a wide area network (WAN), an Ethernet within a building, or an intranet among several geographic locations of a corporation, for example, are contemplated. Also, such signals may be routed wirelessly through WiFi or Bluetooth adapters.

The system/device may also include a calendar and scheduling component in order to alert the remote patient of various events. For instance, if a caregiver is scheduled to visit on specific days and/or at specific daily times, then the computer may be programmed with such reminders that can be easily conveyed to the remote patient, either through a video or audio reminder (with a repeated display of either or both types until the remote patient acknowledges receipt of such a reminder) until the actual event occurs (with intervals of reminders set as desired for such a purpose). Reminders ahead of time may be provided as well of such visits/events and such a reminder activity may also act as a suitable well-being acknowledgement for the remote patient in certain circumstances, if desired. Likewise, such a scheduling component may be utilized for authorized outside parties to remotely add their own scheduled visits on demand, thereby taking advantage of such a reminder system to allow for proper notification of such an upcoming event for the remote patient, too. In essence, such an added system benefit may be utilized for any purpose, including scheduled doctor appointments (and the like), times to prepare for shopping trips (and the like), and any other event that would allow for reminders in such a manner (and thereby allowing for memory stimulation through such a system, as well).

A camera may also be mounted on the device (for any number of reasons, including the communication capability alluded to above) in order to allow for an outside party to view the surroundings of the remote patient if needed. Although a minimal level of invasiveness in envisioned with this overall system/device, if the remote patient is in need of an extra level of security to such an extent, such a camera (like a web cam, for instance) may be utilized as an extra means of monitoring in addition to its utilization as a communication device.

Thus, in total, the overall device/system/method allows for a combination of memory stimulation and notification to outside parties of the condition of a remote patient without any need for such a patient to hit any type of panic button. Such a passive system/method thus provides both a therapeutic benefit and a reliable safety notification procedure without treading on the independence of an otherwise healthy and self-sustaining patient.

Although such a device/system is envisioned primarily for the benefit of persons with early onset dementia and other like conditions, in actuality it may be utilized in any number of situations, both in terms of types of patients and in locations wherein such a system may be useful. Certain elderly patients may not exhibit dementia symptoms, but may need monitoring to ensure their health and safety are not compromised. Utilizing a friendly reminder system including video clips and pictures and then instructions for such a purpose would also be effective in such situations as the interest of outside parties as to status of such elderly persons without having to call or otherwise travel on a daily basis to such a location may not be possible. As such, a notification in conjunction with a friendly greeting to such an extent would be inviting and helpful, particularly in terms of having the remote patient (an elderly person in their own home, in such an instance) properly respond by the same type of notification system. Likewise, such systems/devices may be placed in classrooms to provide a message to a teacher (surreptitiously, for instance, such as under a desk) asking about the conditions present at that moment. If a reply is not received within a certain amount of time, then a proper message may be generated to school officials that problems may be occurring that require further attention. As above, too, such a system/device may be utilized within a nursing home facility for placement in individual rooms, particularly as a means to allow for daily, or even hourly (as examples) presentations to patients therein including familial videos and/or pictures, with the ability for the patient to then communicate with the facility nurses/officials that their condition is acceptable at that moment. The same could be used in community living centers in much the same way. Basically, the overall device/system/method may be employed in many different situations with the primary utilization concerned with the capability of providing a therapeutic benefit to early onset dementia patients through the presentations of memory stimulation activities as noted above. The versatility of the overall system/method accords highly effective and reliable sharing, enjoyment, and safety for the users/patients in any location/milieu.

DETAILED DESCRIPTION OF THE DRAWINGS

Without any intention of limiting the scope of the inventive system/device/method, the drawings described herein provide but one embodiment herein. Various modifications and different configurations of such a system/device/method may be employed without deviating from the scope and basis of the present invention.

Figure 1:
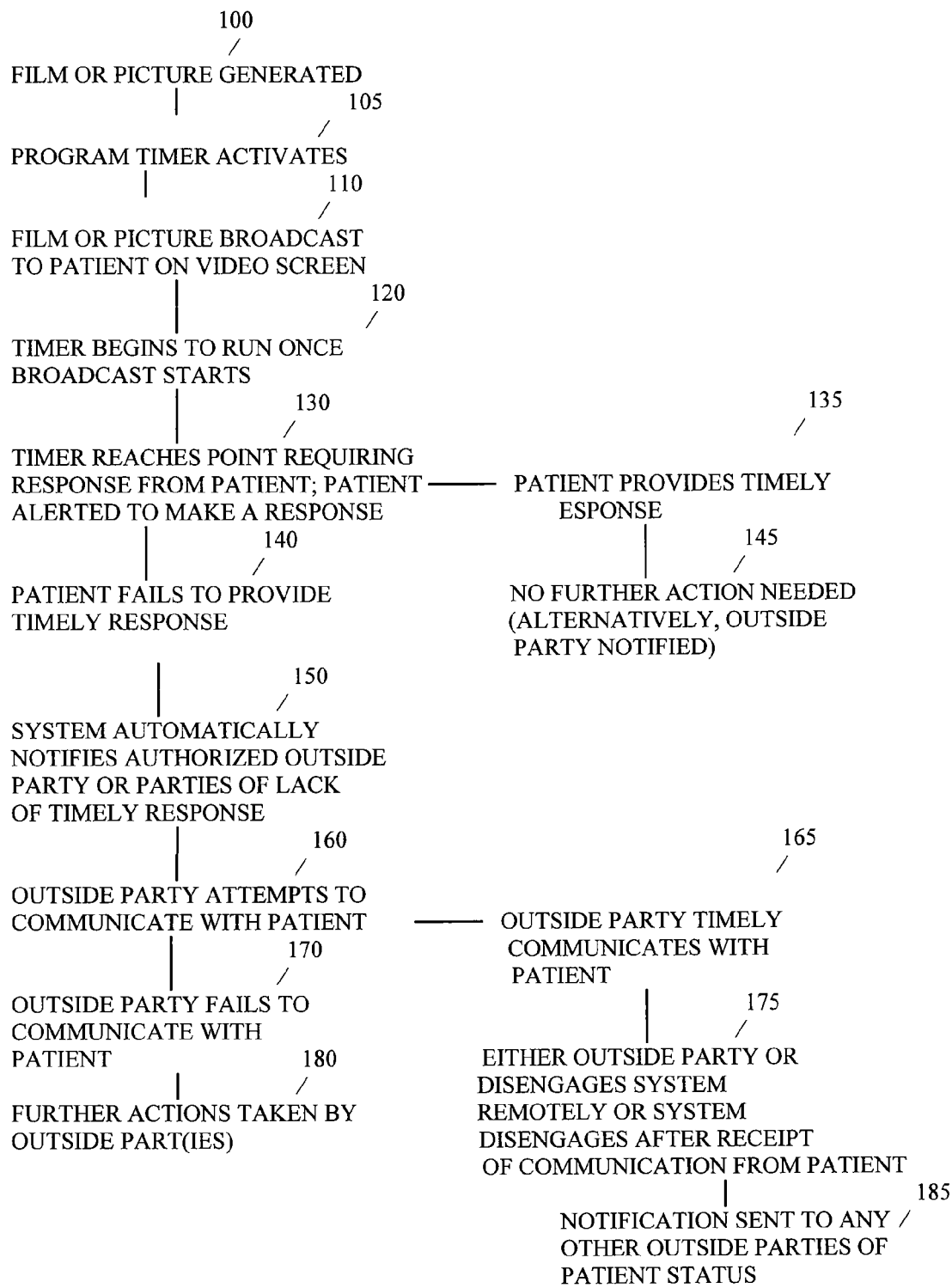
FIG. 1 depicts a flow chart showing the overall system/method of the invention.

FIG. 1 shows a standard flow chart of the overall video presentation/status notification method of the instant invention. As noted above, the overall system/method provides a dual functionality, at least, as a manner of providing memory stimulation to a person/patient while simultaneously serving as a means to allow for such a person/patient to timely notify concerned outside parties of their health and/or safety status. This is accomplished through a device (as described in greater detail in FIG. 2) that includes a video screen and various components to provide such beneficial capabilities. The overall method, then, includes the initial generation of a film or picture 100 (or a combination of both or a set of multiple films or pictures) in combination with, if desired a soundtrack of some type. Such a film or picture 100 (or more, as indicated) is provided in such a manner through any number of procedures, including, without limitation, downloading from a camera (or through a memory card, or like device, as one non-limiting example), transfer from a computer device (such as, again, as one non-limiting example, a thumb drive or even an email, basically any type of signal that may be transferred in such a manner), and the like. Such a film or picture (or both) 100 can be generated by an outside party and inputted within the broadcast device either in a delayed fashion or, if desired, instantaneously, if the proper connections and uploading/downloading system is in place for such an undertaking. In essence, though, the film or picture (or more) generation 100 is provided in order to have a proper mode of stimulating the memory of the subject person/patient to whom such a film or picture 100 is to be broadcast 110 via the inventive system/device. Prior to the broadcast of such video or picture 110, a program timer is initially activated 105 that alerts the patient that such a broadcast is ready to start. Such a timer may ring as a telephone, or provide a musical riff or line, or, if the patient is hard of hearing, the screen may light up or flash to get the patient's attention, not to mention, the system may be connected with a remote device that vibrates, lights up, or plays a musical line, while held by the patient; basically, any notification means that is conducive to alerting the patient that the broadcast is to start may be employed. Thus, upon proper notification 105, such a broadcast step is performed 110 on a video screen for a person/patient to view. Furthermore, as alluded to above, such an alert/timer may be part of a regimen of memory stimulation therapy at specific time intervals in order to maximize and/or optimize the overall benefits of such a memory stimulation procedure for the subject person/patient. Upon initiation of the broadcast, and thus presumably upon proper notification to the subject person/patient that such a broadcast has started, a timer of some type begins to run 120. The purpose of such a timer 120 is to correspond to the overall time frame of the broadcast presentation 110 in order to eventually allow for the subject person/patient to notify outwardly through the overall system that viewing of such a broadcast has taken place. Additionally, though, such a timer step 120 leads to a further indication step 130 by the system to alert the subject person/patient both that notification of their status should be initiated and how such notification should be made 130. In this manner, the subject person/patient thus not only has the benefit of a memory stimulation exercise through the broadcast of a film, picture, etc. 110, but also the further benefit that instructions for notification and provided via the broadcast device 130 and that if such are understood then notification thereof 135 provides comfort to outside concerned parties that such a person/patient's health and/or safety status is acceptable. Thus, once the alert and instruction to notify is made 130, the subject person/patient may then obey the commands made thereby and provide a timely response through the device itself 135. Such a notification may be made through any number of means, however, for simplicity, as one potentially preferred, non-limiting embodiment, the subject person/patient may simply depress a properly colored button on the video device (50 of FIG. 2) (such as a lit green button, as one example) to convey that such a person/patient is safe and secure and understands the instructions provided during the memory stimulation exercise. If such a action is undertaken by the subject person/patient 145, then the system may either remain idle in terms of any further activity and specifically in terms of any further notifications provided to any outside parties of the situation concerning the subject person/patient, or the system may provide simple notification of some type (such as, as one non-limiting example, a simple email or generated text or generated call to an outside party or parties) that the subject person/patient is fine.

However, any failure to provide a proper response 140 subsequent to the subject person/patient alert step 130, and particularly within a time frame that provides a suitable period for such a person/patient to review and understand the memory stimulation exercise and the instructions for status notification provided therewith 130 (for example, within 30 seconds to about 2 minutes of expiration of the broadcast and instructions provided therewith), then the system automatically generates notifications 150 to all authorized outside parties that such a lack of timely response 140 has occurred. Such notifications 150 may be of any type, as discussed previously, including phone calls, emails, texts, and the like, that are sent directly to such outside parties 150. At that point, any such outside party may then attempt to contact the subject person/patient through the system (10 of FIG. 2) or through another means (such as a telephone, although the system will include a means to directly contact such a person/patient via the video screen and amplifier present therein, such as 85 and 85A in FIG. 2) in order to assess the situation from a remote position. If the outside party is able to communicate with the subject patient/person 165, then the outside party may disengage the notification system or the system may be programmed to disengage once a response is received from the remote patient 175. Once either result is achieved, the system may then provide further updates to any other outside parties as the subject person/patient's status 185. If the outside party is then unable to communicate with the subject person/patient 170, then any further actions may be undertaken (communication with proper authorities, such as police, ambulance, and the like, services) 180 in order to best ensure the safety and well-being of the subject person/patient.

Subsequent to such a cycle of activity, as discussed previously, the system/device may be configured to provide a set regimen of memory stimulation exercises (and thus notification requests) at specific time intervals. However, if desired, such a system/device may be activated remotely by an outside user in order to provide an effective check-in procedure from a remote location, as well. Thus, the overall method may be employed on-demand, rather than with a stringent and set schedule.

Although such a system is primarily designed as a dual memory stimulation/health and safety status notification system/device, as noted above, such a system may also utilize the overall structure and platform to provide a calendar and thus schedule notification procedure for a subject person/patient, including a means to alert such a person/patient as to upcoming visits from certain people and/or trips to certain locations (grocery shopping, doctor's offices, and the like). To that end, the device may be properly programmed and accessed by authorized outside parties to input such information and then, within a certain time of a scheduled event, the device/system may remind the subject person/patient of such an upcoming appointment.

Figure 2:
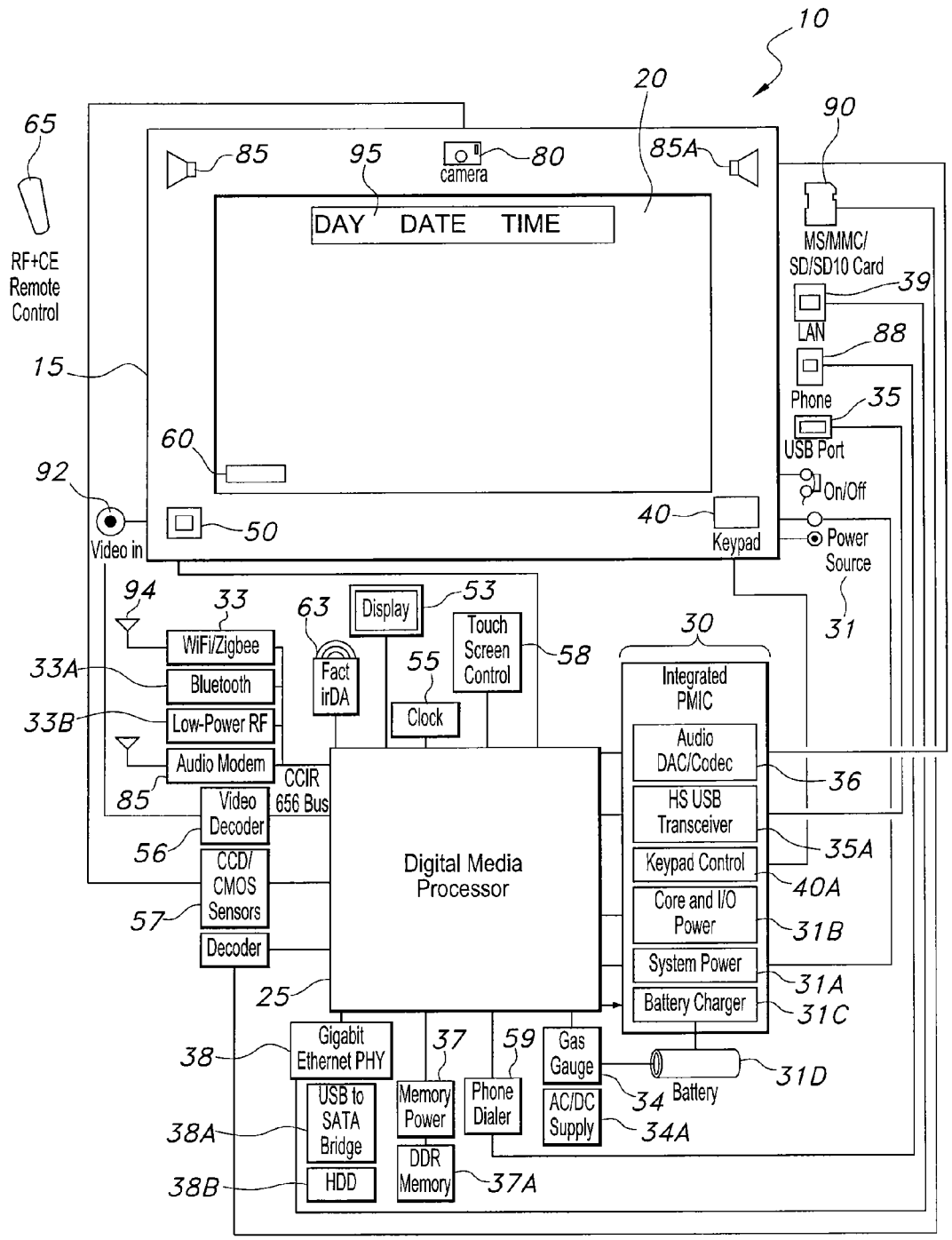
FIG. 2 depicts a view of the inventive system/device in relation to a schematic with the various components.

FIG. 2 thus provides an overview of one potentially preferred embodiment of the inventive system/device 10. An LCD video screen 20 is present within a console 15 and receives and displays data from a video processor 25 via a USB Flash Drive 35, 35A, internal memory source 37, 37A, ethernet connection 38, 38A, 38B, wi-fi network (Zigbee, Bluetooth, low-power radio frequency system, as examples) 33, 33A, 33B, and other cellular source (LAN, for instance, 39). The screen 20 is connected to the communicator control panel through base electronics and support circuitry 30, including power controllers 31, 31A, 31B (and battery charger 31B and battery 31D, in case the power supply is disconnected or fails during an outage), power supply components 34, power gas gauge 34A, at least one random access memory device 37, 37A, and at least one audio card component 36. Processors and input output controllers encoders/decoders. A keypad (or keyboard) 40 is supplied as alphanumeric (standard telephonic or QWERTY, as examples) for communication with an outside entity from the device itself, with a keypad control component 40A within the base electronics 30. As well, an alert button 50 is provided for quick notification of any problems, as well as the potential for the remote patient to provide an effective response to the inquiry set forth during the therapeutic video presentation (not illustrated) as well. A reset button 60 is present either on the screen 20 (as here) or on the console 15 as well that allows for the entire system to be restarted if the remote patient indicates a problem or fails to provide a suitable response timely subsequent to the video presentation. Such buttons 50, 60 but may also be levers, switches (such as membrane switches, toggle switches or the like), touch sensors (including portions of a touch screen), or the like in other embodiments at the discretion of the device designer. The screen 20 further includes a DAY/DATE/TIME box 95 that continuously provides the remote patient with such information. The DAY is thus the specific day of the week (Monday, Tuesday, etc.); the DATE is provided in Month/Day/Year format (thus, Apr. 23, 2011, for instance); the TIME is provided in typical or military time (depending on the desire of the user) (most preferably, though, in typical time format as, for instance, 5:00 PM). Such information is updated as needed through a suitable internal clock mechanism that functions with battery power, if necessary, and is self-correcting for any time changes (such as standard time changed to daylight savings time, as one example). As well, such a box 95 is suitably lit to provide such information at any brightness level even in a dark room. Thus, the remote patient is provided such information continuously for whatever needed reason or purpose.

The video screen 20 is, again, connected via a digital memory system processor 25 that stores other data and circuitry to operate the system in total. Such contains clock circuitry 55, touch screen controls 58, camera sensors 57, a video display control 53, a video decoder 56, a phone dialer 59 and a remote control system 63 (and thus the overall system 10 may be activated through a remote control device 65, and digital support circuitry for such purposes. Such a processor 25 thus sends and receives programming through appropriate channels to and from the remote patient as needed and on demand. As noted above, a USB Port 35 receives video from a memory source (such as a flash drive, for instance), as well.

The console 15 will further include a camera 80 for video and photographic transfers and presentation possibilities on the screen 20 as well as to send to offsite individuals. Speakers 85, 85A are included to allow for communication with offsite individuals directly to the remote patient through a phone component 88 (for connection purposes). The video device 80, as well as the audio speakers 85, 85A are further enabled for wireless communication potential out from the console 15 through a proper SD/SDIO card 90, if needed. Video is also controlled into the console 15 through a decoder 56 and a port 92, allowing for external messages to be sent to the remote patient in such a fashion. The phone dialer 59 is included to deliver urgent messages to a responsible party in case the remote patient fails to provide a suitable acknowledgement to the therapeutic memory inducing presentation. As noted above, if too much time elapses subsequent to the initiation of such a presentation without notification from the remote patient, such a system automatically starts to provide the necessary communications to such interested outside parties. Once verification of status is received, however, any outside interested party may, again, shut down the system remotely; alternatively, once status is confirmed, the remote patient may also restart the system through the alert/restart button 60.

Thus, in operation, the cellular transceiver 86 processes cellular signals received remotely (through an antenna 94, wi-fi 33, and the like 33A, 33B) and delivers program data to the processor 25. Such a device thus transmits program data from the processor 25 to a cellular tower (or like device)(not illustrated) for communication benefits. The phone 88 may also be present and allowed to connect to a house phone (not illustrated) through a modular telephone cord, if desired.

The screen 20 thus includes a menu of selections for the user (not illustrated) that is activated by a menu button for programming purposes and/or play back of the video presentation on demand by the remote patient. An arrow key thus allows for navigation of the video screen for such a purpose to highlight specific and desired actions.

An ethernet plug 38 is present to connect the unit to a high-speed internet source through a category 5 or 6 cable to a wall jack or modem connected to a LAN 39 (or WAN, not illustrated) network, as well.

Additionally, the device 10 includes the control camera 80 in order to allow for monitoring of the remote patient as well as to record video clip at the station or further allow for communication through a signal sent to and through the video processor 25 (such as via a SKYPE program, and the like).

A wi-fi transceiver 33 is present as well to accept signals from an on-board antenna 94 (or other like device) to decode/encode communications delivered as a signal to the processor 25. The transmitted data may be a video message (presented on the screen 20) or other like presentation for the remote patient's benefit, that is further sent to the wi-fi modem 33 (or other like device 33A, 33B) for connection to the internet or other device located on the premises of the dwelling in which the device is present (not illustrated).

An antenna 94 thus receives transmitted signals from the modem or other wi-fi device 33, 3A, 33B or cellular tower and routes the signal to the processor 25, thereby forwarding the signal to another appropriate cellular or wi-fi transceiver (not illustrated). The antenna 94 receives such a signal in intervals and broadcasts as needed to the wi-fi modem or cellular tower to ensure proper communication is in place for the overall device 10 to function properly and that open communication capability between the remote patient and any outside interested party, as well as the device itself 10 and any outside interested party, in case of any failure of proper status updating or emergency situation occurs.

Lastly, a wireless receiver 33, 33A, 33B processes wi-fi signals from the antenna 94 and encodes them for delivery to the processor 25. Such then further transmits the signal from the processor to any outside interested parties through the antenna 94, as needed.

In this manner, then, a video presentation may be supplied to the device, the remote patient may be alerted to its start, viewing and listening may be provided for such a patient, a request for status indication instruction is given during viewing, if such an indication is not provided timely thereafter, then instant notification to all pre-determined outside interested third parties is initiated, if the remote patient is properly contacted and verifies that safe status is actually in existence then a remote user may then indicate discontinuance of the notification step and the device is reset for a future exercise, or, if the remote patient still does not indicate safe status then an outside interested party may contact an emergency response entity to provide assistance with the remote patient. With a suitable battery-powered backup in place, such an overall system will be available for all interested parties even if an overall power outage occurs, as well. Thus, an effective communication device/therapeutic memory-inducement system is supplied for the benefit of remote patients that wish to remain in their own homes during periods of potential memory loss or other like situations.

Having described the invention in detail it is obvious that one skilled in the art will be able to make variations and modifications thereto without departing from the scope of the present invention. Accordingly, the scope of the present invention should be determined only by the claims appended hereto.

I claim:

1. A combination memory stimulation and status notification communication system for utilization with a remote patient, wherein said system comprises a device including:
    a) a video presentation component comprising at least
        i) a video screen for presenting visual pictures and/or films to a remote patient, wherein said visual pictures and/or films are set to repeat on said video screen, and wherein said visual pictures and/or films include instructions for said remote patient to indicate status notifications at certain times subsequent to presentation of said visual pictures and/or films, and
        ii) a stop or reset switch to permit said remote patient to discontinue the video presentation, wherein activation of said stop or reset switch provides said remote patient status notifications; and
    b) a communication component comprising at least
        i) a communication module to allow for spoken communications to transfer between said remote patient and an authorized outside party, and
        ii) an alarm and signal generator to notify an authorized outside party of the failure of said remote patient to timely activate said stop or reset switch of step a)ii); and
        iii) an override component available to either said at least one authorized outside party or embedded within said system to discontinue said alarm and signal generator upon receipt of a suitable communication from said remote patient subsequent to alarm and signal generator activation.

2. A method of providing a combined remote patient memory stimulation presentation and status notification for a remote patient, said method comprising:
    providing the system of claim 1;
    activating said video presentation component to providing memory stimulation to said remote patient through the utilization of said video screen through the activation of a program including at least one visual picture and/or film;
    subsequently generating instructions within said video presentation component during said visual picture and/or film requesting said remote patient to provide notification of his or her status, said notification provided through activation of said stop or reset switch;
    wherein, if said notification is not timely provided by said remote patient, said system sends a communication of such lack of status notification to at least one authorized outside party; wherein said outside authorized party has remote control to discontinue said notification step upon receipt of a proper communication with said remote patient.

3. The method of claim 2, wherein said system is provided within the dwelling of said remote patient.

\* \* \* \* \*